US008747746B2

(12) United States Patent
Lefebvre

(10) Patent No.: US 8,747,746 B2
(45) Date of Patent: Jun. 10, 2014

(54) AUTOMATED SYSTEM AND METHOD OF PROCESSING BIOLOGICAL SPECIMENS

(71) Applicant: Sakura Finetek U.S.A., Inc., Torrance, CA (US)

(72) Inventor: Gilles Lefebvre, San Clemente, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 0 days.

(21) Appl. No.: 13/768,953

(22) Filed: Feb. 15, 2013

(65) Prior Publication Data

US 2013/0164781 A1 Jun. 27, 2013

Related U.S. Application Data

(62) Division of application No. 12/979,666, filed on Dec. 28, 2010, now Pat. No. 8,388,891.

(51) Int. Cl.
*G01N 21/00* (2006.01)

(52) U.S. Cl.
USPC .......... 422/65; 422/63; 422/64; 422/66; 422/67; 422/536; 436/180

(58) Field of Classification Search
USPC .......... 422/536–537, 63–67; 436/180
See application file for complete search history.

(56) References Cited

U.S. PATENT DOCUMENTS

| | | | |
|---|---|---|---|
| 4,190,472 A | 2/1980 | Slonicki | |
| 4,537,648 A | 8/1985 | Shiino et al. | |
| 5,700,346 A | 12/1997 | Edwards | |
| 6,076,583 A | 6/2000 | Edwards | |
| 6,745,916 B2 | 6/2004 | Plank et al. | |
| 6,821,072 B2 | 11/2004 | Thiem et al. | |
| 7,153,474 B2 | 12/2006 | Thiem | |

(Continued)

FOREIGN PATENT DOCUMENTS

| | | | |
|---|---|---|---|
| EP | 1811281 A2 * | 1/2007 | |
| EP | 1811281 | 7/2007 | |

(Continued)

OTHER PUBLICATIONS

Sakura Finetek, Non-final Office Action mailed Apr. 25, 2012 for U.S. Appl. No. 12/979,666.

(Continued)

*Primary Examiner* — Jyoti Nagpaul
(74) *Attorney, Agent, or Firm* — Blakely Sokoloff Taylor & Zafman LLP

(57) ABSTRACT

An apparatus including at least one of a stainer module and a coverslipper module; an imaging module; a storage module; an automated transport module for transporting at least one slide between at least one of the stainer module and the coverslipper module, the imaging module and the storage module; and a controller. A method including processing at least one slide; determining whether an imaging module is available for imaging of a biological specimen on the at least one slide; transporting the at least one slide to the imaging module using an automated transport module; and transporting the at least one slide to a storage module using the automated transport module when it is determined that the imaging module is not available. A system including a processing module for processing at least one slide including a biological specimen thereon. A machine readable medium.

24 Claims, 9 Drawing Sheets

(56) References Cited

U.S. PATENT DOCUMENTS

| | | |
|---|---|---|
| 7,226,788 B2 | 6/2007 | De La Torre-Bueno |
| 7,271,006 B2 | 9/2007 | Reinhardt et al. |
| 7,303,725 B2 | 12/2007 | Reinhardt et al. |
| 7,368,081 B2 | 5/2008 | Thiem |
| 2003/0049172 A1 | 3/2003 | Thiem |
| 2003/0163031 A1 | 8/2003 | Madden et al. |
| 2006/0239868 A1 | 10/2006 | Sage et al. |
| 2006/0243199 A1 | 11/2006 | Kiene |
| 2007/0172100 A1 | 7/2007 | Lefebvre |
| 2008/0029218 A1 | 2/2008 | Reinhardt et al. |

FOREIGN PATENT DOCUMENTS

| | | |
|---|---|---|
| GB | 2387652 | 10/2003 |
| WO | WO-9520176 | 7/1995 |
| WO | WO-9703827 | 2/1997 |
| WO | WO-0037986 | 6/2000 |

OTHER PUBLICATIONS

Sakura Finetek, Final Office Action mailed Sep. 6, 2012 for U.S. Appl. No. 12/979,666.

* cited by examiner

AUTOMATED SYSTEM AND METHOD OF PROCESSING BIOLOGICAL SPECIMENS

CROSS-REFERENCE TO RELATED APPLICATION

The application is a divisional of co-pending U.S. patent application Ser. No. 12/979,666, filed Dec. 28, 2010 and incorporated herein by reference.

BACKGROUND

1. Field

An automated system of processing biological specimens.

2. Background

In various settings, examination of biological specimens is required for diagnostic purposes. Generally speaking, pathologists and other diagnosticians collect and study samples from patients, and utilize microscopic examination, and other devices to assess the samples at cellular levels. Numerous steps typically are involved in pathology and other diagnostic process, including the collection of biological samples such as blood and tissue, processing the samples, preparation of microscope slides, staining, examination, re-testing or re-staining, collecting additional samples, re-examination of the samples, and ultimately the offering of diagnostic findings. Numerous medical or veterinary personnel may be involved in the diagnostic processes, including surgeons, phlebotomists or other operating personnel collecting samples, pathologist, histologists and other personnel processing, transporting and examining the samples and so on. The complexity of the tissue handling procedures from the operating room to the laboratory and back to the diagnosticians or surgeons have become increasingly complex in large medical environments where high volumes of samples need to be handled, processed and examined on a daily basis.

Various steps of the tissue handling procedures have been automated using instruments each of which typically are controlled by a dedicated computer or an on-board computerized controller. In some laboratories, information can be shared between automated instruments and/or a networked laboratory or hospital information system, such as to store patient or tracking data. One example of an automated instrument is an automated tissue processing system in which biological samples are fixed and infiltrated with paraffin in an automated fashion. Exemplary tissue processing systems are the TISSUE-TEK® VIP® and the TISSUE-TEK® XPRESS® processing systems available from Sakura Finetek U.S.A., Inc. of Torrance, Calif.

Another example of automation is an automated microscope slide stainer and coverslipper, which stains microscope slides and applies coverslips to the slides in an automated fashion. Examples of such automated staining and coverslipping systems are TISSUE-TEK® PRISMA® and TISSUE-TEK® FILM® combo system and TISSUE-TEK® PRISMA® and TISSUE-TEK® Glas™ g2 combo system available from Sakura Finetek U.S.A., Inc. of Torrance, Calif.

Despite the assistance of automated instruments, pathologists, other diagnosticians and laboratory personnel typically must be involved in numerous steps during the processing and examination of biological samples. For example, once a sample has been stained, the stained sample on a microscope slide may be physically examined under a microscope. This typically involves transport of the microscope slide to a diagnostician who is located outside the laboratory, or in other cases may involve a diagnostician going to the laboratory to examine the microscope slide. Alternatively, the stained sample on a microscope slide is imaged with a digital camera and the image of the sample is uploaded for examination by a diagnostician.

Following this initial examination step, the diagnostician evaluates whether additional testing is required. Such additional testing might involve collecting further samples from a patient, or further testing of samples already collected. For example, the diagnostician may require that the existing sample be sectioned further and a different staining regimen or other protocol be applied. This can result in iterations of one or more of collection, grossing, processing, infiltration, embedding, sectioning, coverslipping, staining, examination etc. In addition, different coverslipped slides may require different drying times. Accordingly, some slides may be ready for examination while others are not. All of this can result in time delays, as well as tissue impairment. Following the iterations of additional tests and procedures, the pathologist repeats the examination process, and may then request still further tests in an iterative fashion until an ultimate finding is reached. Even with automated instruments in these processes, there are numerous transport, and human interventions required.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

DETAILED DESCRIPTION

In the following paragraphs, the present invention will be described in detail by way of example with reference to the accompanying drawings. Throughout this description, the preferred embodiments and examples shown should be considered as exemplars, rather than as limitations on the present invention. As used herein, the "present invention" refers to any one of the embodiments of the invention described herein, and any equivalents. Furthermore, reference to various aspects of the invention throughout this document does not mean that all claimed embodiments or methods must include the referenced aspects.

Figure 1:
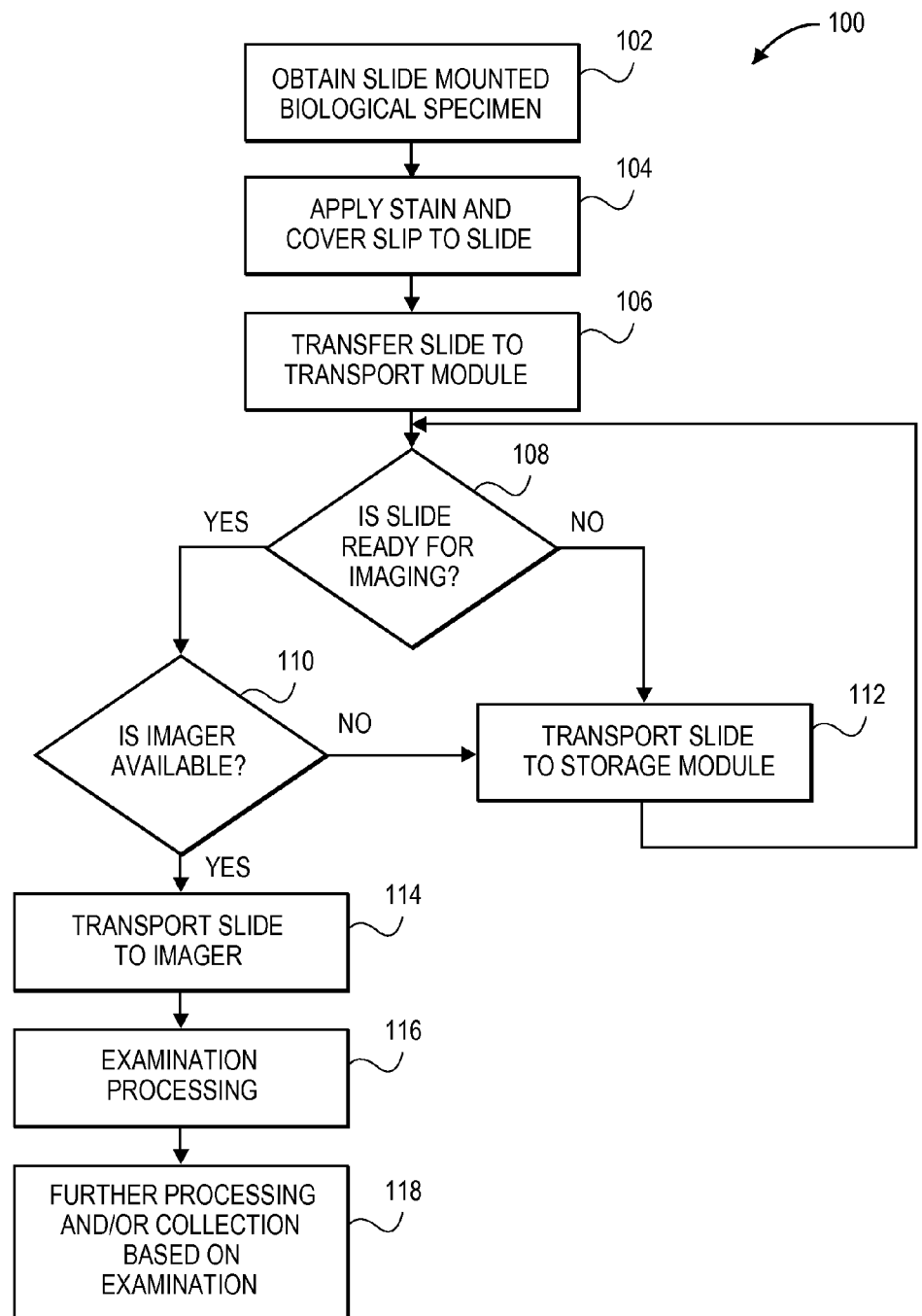
FIG. 1 is a flow chart of one embodiment of a method for automatically processing biological specimens.

In overview, a system and process for performing a series of automated operations including tissue processing, imaging and tissue storage is disclosed. FIG. 1 shows a flow chart of one embodiment of a process implemented by a system (i.e., machine-readable program instructions implemented in a processor connected to process control modules). As illustrated in block 102, process 100 includes obtaining at a material handling system a biological sample that has been mounted on a slide. The biological sample is conveyed to a material handling system, for example by manual transport, a cart or automated transport. In a hospital embodiment, the specimen may be delivered to a medical laboratory, whether on-site or at a remote location.

At the material handling system, the slide mounted specimen may be processed via automated operations into a condition suitable for a desired examination. In one embodiment, processing includes staining the biological sample and applying a cover slip to the slide (block 104). Staining of the specimen may be optional. The slide having the specimen thereon is then transferred to a transport module (block 106). In some embodiments, the slide is transferred to the transport module using a robotic transferring device as will be discussed in more detail in reference to FIGS. 4-9.

Process 100 further includes determining whether the slide is ready for imaging (block 108). Such a determination may be based on, for example, the drying time of the slide. For example, different methods of coverslipping exist and each one requires different drying times. Representatively, a glass cover slip may require about a day to dry while a film cover slip may dry in about an hour. In this aspect, coverslipped slides that are not ready (e.g. not dry) for further processing (e.g., imaging) are transported to a storage module to give them additional time to dry (bock 112). Slides that are dry are determined to be ready for imaging.

Process 100 further includes determining whether the imager is available for imaging (block 110). Imaging of a specimen on a slide typically takes longer than the amount of time it takes to stain, coverslip and dry the slide, because imaging must be done on individual slides (i.e., one at a time) while staining and coverslipping operations may be done on a number of slides at the same time (e.g., staining a batch of slides). For example, slide imagers can perform a 20× scan of a 15×15 mm tissue in about 2½ to 3 minutes. Higher resolution and z-stacking requirements can double that time. This equates to an imager throughput of from about 10-24 slides per hour. In contrast, up to about 500 slides per hour may be processed through a coverslipper and/or stainer. As a result, the imager is often times not ready to image each of the slides as they exit the coverslipper and/or stainer. If the imager is not available, the slides are transported from the coverslipper to a storage module for storing until an imager is available (block 112).

Once the imager is available, the slide is transported to the imager (block 114) for imaging. At the imager, a digital image of the specimen is captured and stored in a computer memory. After a specimen, or group of specimens, is prepared for examination, the specimen(s) may be examined and the data may be made available to a diagnostician and/or an optional interpretation module which automatically interprets the data (block 116). It should be noted that, as used herein, "diagnostician" refers to any person who may wish to view image data, such as pathologists, surgeons, nurses, researchers, technicians and administrators.

Image data may be created, such as using a digital imager including, for example, a CCD technology. The image data preferably is made available for access by a diagnostician if desired, and optionally the diagnostician is notified such as by electronic notification, such as by an e-mail, computer screen pop-up announcement, banner announcement, pager message or automated phone call. In other embodiments, the image data may also be accessed, or otherwise made available, to an optional interpretation module. The interpretation module may conduct digital processing, such as by using pattern recognition technology in order to develop a preliminary diagnosis, and generate instructions or recommendations for additional processing.

The additional processing, illustrated with block 118, may include collecting additional biological samples, or performing further processing on samples already collected such as running additional or different test procedures or staining protocols. For example, after imaging, a specimen may be transported by the transport module to the storage module. The specimen image may be examined, and if it is determined that further imaging is necessary, the specimen is retrieved from the storage module by the transport module and transported to the imager for imaging. Examination, imaging and interpretation of the sample may be continued until the system or diagnostician deems it to be complete. These repeated tests and examinations are referred to herein as iterative processing, testing or examination. In another aspect of the invention, the diagnostician may access reports that are based on the comparison data created by the interpretation module. In a further aspect of the invention, the diagnostician may order or conduct further iterative processing, testing or examination.

FIGS. 2-9 illustrate examples of automated systems for processing biological specimens. In these figures, information pathways are illustrated with solid lines and/or arrows and material pathways are illustrated with double lines and outlined arrows. As used herein, "material" refers to any biological material including histological and cytological specimens that may be examined in a medical, autopsy, veterinary or research laboratory procedure. The biological material may include tissue samples or specimens, and/or biological fluids such as blood, plasma, etc. Although the illustrated examples are described in relation to tissue, the described systems and methods are not so limited. As used herein the biological material will be referred to interchangeably as a specimen, sample or material. In addition, references relating to processing of a "slide" herein refer to a slide having the biological material thereon.

In the illustrated examples, the material pathways represent examples of transport paths that may be traveled by a physical sample in a laboratory or hospital. A typical progression of the material from one station or system component to the next is depicted by the direction of the arrow. However, it should be understood that the processing stations are provided as examples, as are the directions of material flow. It shall be appreciated that more, fewer or other processing stations may be used in practice of the present invention, and/or more, fewer or other material paths and directions may be used in the practice of the present invention. In addition, the stations may be in any order and any orientation (e.g. vertically stacked or side by side).

Any form of transport may be used that is sufficient to automatically transport the material as indicated by the material pathways. For example, material may be transported by a robotic device from one station to the next as will be discussed in more detail in reference to FIGS. 4-7. The term robot or robotic is to be interpreted broadly as a conveyance, transfer device, electro-mechanical transfer device or mechanism, or automatically controlled, reprogrammable, multipurpose manipulator programmable in three, four, or more axes. The robotic device may take various forms or configurations, consistent with its intended purpose. The robotic device may be programmed with an application program, program routine, or other set of instructions. The program or set of instructions may specify one or more operations the robotic device is to autonomously or at least semi-autonomously perform. Representatively, the program or set of instructions may specify the movements (e.g., coordinates, distances, directions, etc.), timing or triggers, and like information associated with the operations. In some embodiments, the material may also, or alternatively, be hand carried from one station to the next. Additionally, one machine may perform multiple steps with no physical movement of the material from one station to another being required.

Figure 2:
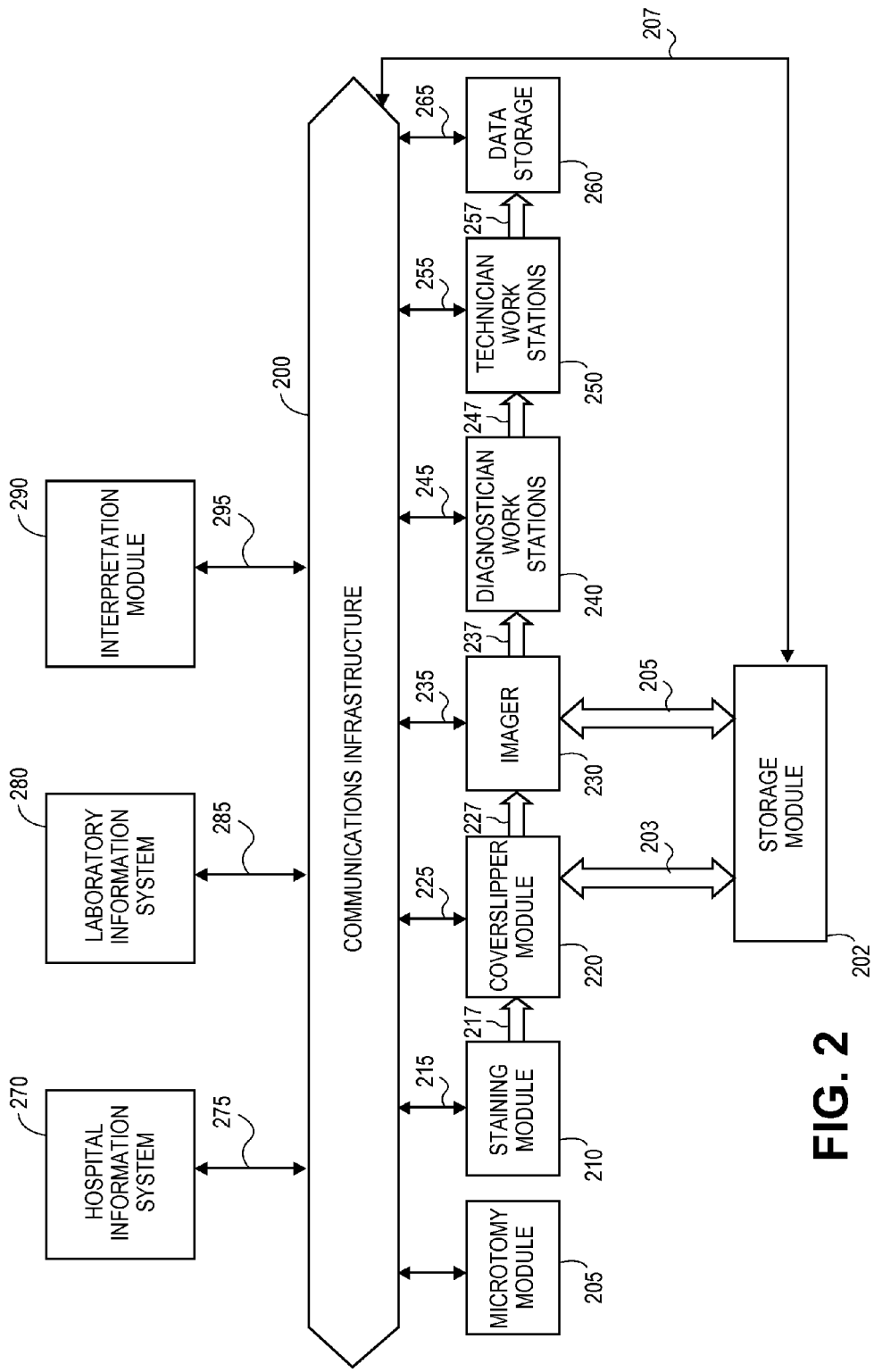
FIG. 2 illustrates one embodiment of an automated system for processing biological specimens.

In the embodiment of FIG. 2, a specimen mounted on a microscope slide is transported to staining module 210. Prior to transporting the specimen to staining module 210, the specimen may be processed through, for example, a grossing station (in the case of non-fluid specimens), a tissue processor where the specimen is treated with a series of reagents, an embedding station where it may be infiltrated with paraffin and embedded and a microtome station where the specimen is sectioned. Specimen sections created in the microtome station are positioned on the microscope slide. Slides requiring deparaffinization may be placed in an oven prior to staining, or placed directly in the stainer if the stainer is equipped with a built-in oven or can perform a chemical deparaffinization step.

Any staining or other test protocol may be performed by the staining module 210 as desired. In one embodiment, an automated stainer is used. In an example, staining with hematoxylin and eosin ("H & E") is performed in staining module 210. Other staining methods such as special stains (SS), immunohistochemistry (IHC), and in situ hybridization (ISH) can also be performed.

In one embodiment, following staining, the samples may be transported along material path 217 to coverslipper module 220 to be coverslipped.

After staining and/or coverslipping, the slide may proceed to imager 230 or storage module 202. In some embodiments, where it is desirable for imaging of the slide to be delayed, the slide is transported to storage module 202 for storage until imaging is desired. Representatively, different methods of coverslipping exist and each one requires different drying times. Coverslipped slides that are not ready (e.g. not dry) for further processing are transported to storage module 202 along material path 203. Once the slides are ready, they may then be transported along material path 205 to imager 235. In this aspect, the differences in drying times from slide to slide are automatically resolved by the automated system.

In some embodiments, the laboratory can select delay criteria based on the coverslipping technique used and the type of sample (histology v. cytology, monolayer slides v. smears, etc.). For example, the laboratory may determine, based on the coverslipping technique to be used and the type of sample on the slide, that the slide should be stored for a period of time prior to imaging. This information may be contained in an identifier associated with the slide. Examples of identifiers include a radio frequency identification (RFID) tag, barcode that may be read by a reader associated with the system that provides information to the automated system. The automated system may read the identifier and follow the assigned processing protocol. In this aspect, after coverslipping, the slide is transported to storage module 202 and stored for the predetermined period of time. After such time, the system may alert the transport module to retrieve the slide from storage module 202 and transport the slide to imager 230 for imaging.

In addition to drying times, the availability of imager 230 may further delay imaging. In particular, imaging of a specimen on a slide typically takes longer than the amount of time it takes to stain, coverslip and dry the slide. For example, current commercially available slide imagers can perform a 20× magnification scan of a 15×15 mm tissue in about 2½ to 3 minutes. Higher resolution and z-stacking requirements can double that time. This equates to an imager throughput of from about 10-24 slides per hour. In contrast, up to about 500 slides per hour may be processed through the stainer/coverslipper modules. As a result, the imager is often times not ready to image each of the slides as they exit the stainer/coverslipper modules. The identifier associated with the slide may store information regarding the desired imaging protocol for the slide (e.g., a 10× scan, a 20× scan or a 40× scan). Upon reading the identifier, the system schedules imaging of the slide with an imager capable of imaging at the desired magnification. If the desired imager is not available when the slide is otherwise ready for imaging, the slide is transported from staining module 210 and/or coverslipper module 227 along material path 203 to storage module 202 for storing until imager 230 is available.

It is further contemplated that after a specimen is imaged by imager 230, the specimen slide may be transported along material path 205 to storage module 202. The slide may be stored in storage module 202 for future testing and/or examination.

Once the specimen is ready for imaging, at least one image of the material specimen is obtained by imager 230. The imaging protocol for each slide which is to be followed by imager 230 may be flexible and can be defined at any time by, for example, the diagnostician (e.g., pathologist). In this aspect, the diagnostician can have real time control of the imaging process remotely. For example, a pathologist may examine an image and determine that additional images of the slide are necessary. Representatively, the pathologist may determine that images at a different magnification are necessary or that the imager should focus deeper into a tissue area. According to the automated system disclosed herein, the pathologist may instruct the system to obtain further images. The system will then automatically retrieve the specimen from storage module 202 and transport it to imager 230 for further imaging as requested. The pathologist may receive the results the same day as the request, as opposed to current imaging systems which often process highest resolution and z-stacking images overnight.

Imager 230 may include one or more imagers. The imager can be any system that generates images that can be interpreted manually interpreted or, optionally, automatically interpreted by interpretation module 290. In the illustrated embodiment, imager 230 includes a microscope and a camera capable of recording digital images of the microscope's view field. For example an optical CCD based camera can be used to generate the digital image data. The digital image data can be stored in any fashion that provides for access to the data as required by interpretation module 290, diagnostician work station 240 and/or technician work station 250 and/or as desired by anyone needing access to the image data, such as diagnosticians or laboratory personnel. Examples of suitable data storage are local storage devices associated with imager 230 (such as hard drive, removable memory, flash memory, optical memory such as CD or DVD etc.), and/or networked memory such as diagrammatically illustrated by data storage 260. It should be noted that any form of information may be generated by imager 230, in addition to the image data. For example, imager 230 may optionally associate other types of data, such as a log of patient information associated with the image data and as discussed further herein. Alternatively, another processing system may associate the image data with other data.

In one embodiment, the type of information generated is intended to be sufficient for interpretation module 290 to perform its interpretation processing and generate the desired report. Interpretation module 290 may take any desired form, such as for example, a dedicated computing system, or alternatively it may be a module running on a computing system used for multiple purposes. In additional examples, it may be freestanding, a part of imager 230, part of hospital information system 270, part of laboratory information system 280, or it may be in any location where data may be received from imager 230. Although the figure depicts a single interpretation module 290, it should be understood that plural interpretation modules 290 also may be used. In further examples, diagnostician work stations 245 may include interpretation modules 290 or interpretation module clients that enable the diagnostician to locally conduct an interpretation based on the data available including, without limitation, image data from imager 230.

In the embodiment of FIG. 2, interpretation module(s) 290 is in communication via communications infrastructure 200. Interpretation module 290 may access data as desired, whether directly from imager 230, via data storage facility 260, or via local data storage. Interpretation module uses the image data and other data to perform an analysis and a recommendation. In an embodiment, the analysis includes a pattern recognition analysis in a pattern recognition system of interpretation module 290. In one form of pattern recognition, image data from imager 230 is compared to a database of known patterns. If a sufficient level of correspondence is found, a matching pattern is located upon which a recommendation, diagnosis or further processing instruction can be made. The pattern database can be a part of interpretation module 290, or located externally, such as for example in data storage 260 or laboratory information system 280.

Following imaging by imager 230, interpretation module 290 may be configured to determine if the imaged sample should go to storage module, in which case it proceeds along material pathway 227, or interpretation module 290 may be configured to determine whether the particular sample needs to undergo additional processing, such as that it should go to a diagnostician or other personnel for personal inspection, in which case it proceeds along material pathway 237.

Alternatively, interpretation module 290 may be configured to determine if further processing of the tissue represented by the imaged sample is required. In such case, a new sample of the tissue is necessary for interpretation. In one embodiment, additional section(s) (samples) of the same tissue may have been placed on slide(s) and those slide(s) sent to storage module 202 with a label that links the slide(s) to the imaged sample. In this embodiment, the slide(s) are not stained or coverslipped, and are kept aside. These slides could be identified as being extra sections that should not be stained and kept in the storage area until called back for staining and coverslipping. For example, these extra slide(s) may have the same identification information as the original or primary, perhaps with an additional indicator (e.g., an additional letter or number) to indicate the slide(s) are extra slide(s). If they are not needed, these slides can be discarded after, for example, a user-defined period of time has elapsed or the case has been completed and signed off. Extra sections are cut and extra slides prepared and stained only when there is a requirement for more staining protocols. In an automated handling system that also includes handling of tissue blocks, the request for more staining would be transferred to microtomy module 205. In one embodiment, a tissue block, including a formalin-fixed tissue section in a paraffin block from which another tissue section may have been taken and placed on a slide, includes an identification tag such as a bar code or RFID tag. In response to a signal from a controller, the tissue block is retrieved and transported automatically from a storage module (e.g., storage module 202) to microtomy module 205. The tissue block is stored and may be retrieved by the identification tag. The tissue block would be forwarded to the microtomy area for more sections to be taken.

Representatively, once a new sample is placed on a slide, the new sample proceeds to stainer module 210 where it may undergo operations such as special staining, immunohistochemistry ("IHC"), in situ hybridization ("ISH"), multiplexing or other staining or testing procedures. Subsequently, the new sample may proceed along the material path, for example, back to imager 230. Ultimately it is desired that a tested and imaged sample be stored as indicated by storage module 202. In this example, after inspection by a diagnostician or other person, the original sample may be designated for storage, such as in storage module 202 and the new sample from the same tissue section designated and further processed. The new sample may be processed and inspected and sent to storage The original sample and the new sample are linked by an identification tag. Later, either or both the original and the new sample can optionally be retrieved from the storage module 202, if desired.

The work stations, such as diagnostician work stations 240 or other work stations, such as technician work stations 250 can have any desired structure, including computing systems serving as controllers in communication via communications infrastructure 200 with other processing stations or components of the system. The work stations may optionally also include other components that might be useful in a work area, such as material storage units, furniture, phones etc. In an embodiment, the work stations 240, 250 provide access to information concerning the processing of biological samples, and the results of the processing, including image data from the imager 230 and interpretation data or reports from the interpretation module 290. Technician work station 250 may be in communication with data storage 260 via path 257. In another embodiment, a system may not include work stations such as diagnostician work stations 240 and/or technician work stations 250.

As the material proceeds along the material pathways and through the processing systems, information may be shared between the numerous devices using various information pathways that form communications infrastructure 200. It should be noted that communications infrastructure 200 may be any form of communication system enabling communications between and amongst individuals, computer systems and/or automated processing systems. Representatively, the communications infrastructure may be a computer network that is wired, wireless or a combination of wired and wireless. For example, information access points may be wired into the network and/or joined to the network via a wireless portal. Although the illustrated example shows a networked system in which communications are performed via a network, direct communications also may be conducted. For example in one embodiment, staining module 210 may have a direct communications link with coverslipper module 220 and may access the communications network via a node in coverslipper module 220, or alternatively it may have a direct network link. It should be understood that any suitable communications pathway structure is envisioned which would enable suitable sharing of information between and amongst various stations. Likewise, it should be understood that, in other embodiments, not all of the stations may have a direct communications path. Furthermore, it should be understood that the communication pathways can take any form, such as digital, analog, wired, wireless, paper, oral, telephonic, etc.

In one embodiment, a laboratory network may be provided as the portion of the communications infrastructure 200 between and amongst the laboratory instruments, depicted with reference numbers 210, 220, 230, 202 and also laboratory information system 280 and other work stations 240 and 250 (which might include a computer system such as for example one or more personal computers and/or computer servers). The laboratory network may be networked with a hospital network that is also a part of communications infrastructure 200. In such an embodiment, other devices may have access to the information available on laboratory information system 280 or other laboratory devices via the communications infrastructure 200. Such other devices include for example, diagnostician or administrator work stations 240, hospital information system 270, and in some embodiments interpretation module 290 as well. It should be understood that the flexibility of the information pathways is directed to enable the necessary information flow to track biological samples being processed however desired, and to distribute the necessary information to the appropriate users. Numerous alternative communications system structures may be selected to meet this need, and the illustrated and discussed examples are provided for illustrative purposes only, not to limit the scope or flexibility of the system.

Referring to the illustrated example, communications pathways 203, 205, 207, 215, 225, 235, 245, 255, 265, 275, 285, 295, represent examples of communications pathways between staining module 210, coverslipper module 220, imager 230, storage module 202, diagnostician work station 240, technician work station 250, local or remote data storage 260 and/or hospital information system 270, laboratory information system 280, interpretation module 290, or any other desired station or component of the system.

The sharing of information may be automated, manual or conceptual. For example, information may be shared directly by two machines in communication with each other, it may be made available to a user who can manually input it into another device, or a single machine comprising more than one device shown in FIG. 2 can engage in internal communication. This sharing of information often involves two-way communication. For example, images from a patient having a chronic condition may be sent to a database of patient information storage, and previously obtained information regarding the same patient may be retrieved from the database in order to monitor the progression of the condition. In another embodiment, each station in the material path is capable of communicating via the communications infrastructure 200 and the stations may communicate the progression of the material along the material pathways as well as other information, as discussed in further detail below.

In another embodiment, biological specimens, slides, trays, containers, workpieces, and locations throughout the system may be identified with machine understandable codes, such as provided by RFID tags, shape identifiers, color identifiers, numbers or words, other optical codes, barcodes etc. The identifiers can be recorded to generate data provided to a database, such as data maintained in data storage device 260, by a processor (any computing devices), hospital information system 270, laboratory information system 280 or any combination thereof. Examples of data that may be tracked include patient information and history, information regarding biological sample(s) collected, arrival and departure times of biological samples, tests performed on the samples, processes performed on the samples, reagents applied to the samples, diagnoses made, associated images and so on.

Figure 3:
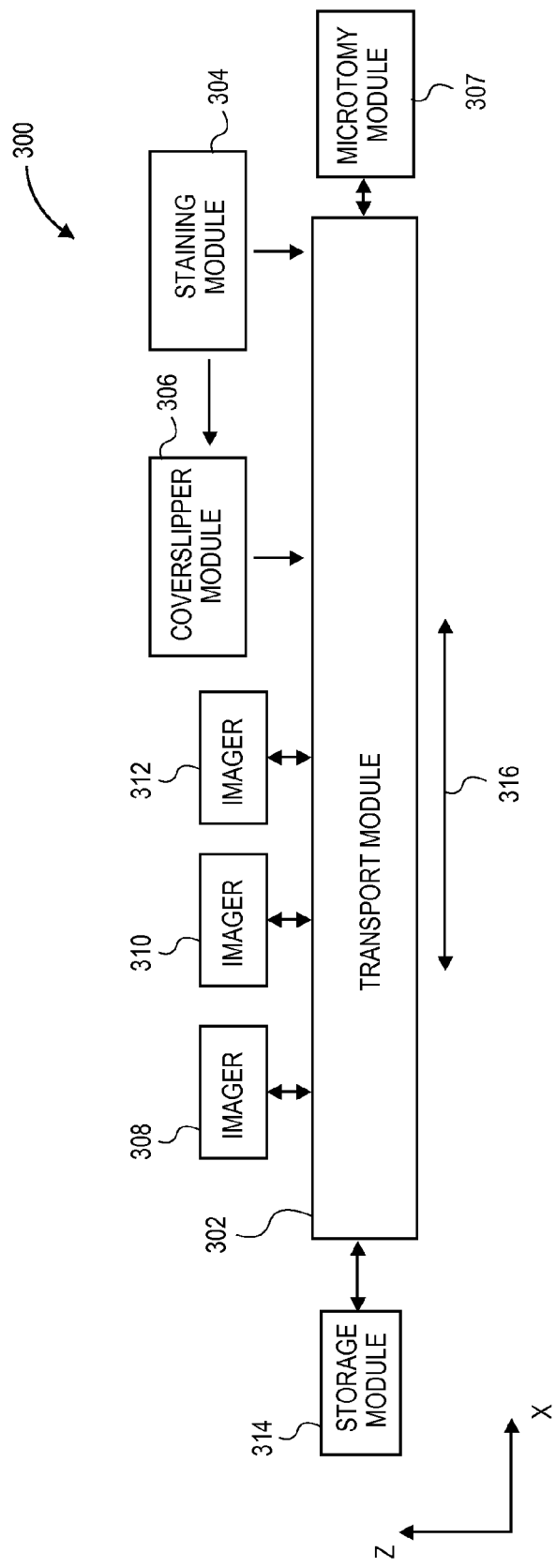
FIG. 3 illustrates one embodiment of an automated system for processing biological specimens.

FIG. 3 illustrates an embodiment of a system for automatically processing a biological specimen. System 300 includes transport module 302. Transport module 302 may automate, or at least partially automate, the transfer of slides or other tissue holders between the stations, namely between one or more of staining module 304, coverslipper module 306, imagers 308, 310, 312, storage module 314 and microtomy module 307. Automatically transporting slides or other tissue holders between staining module 304, coverslipper module 306, imagers 308, 310, 312 storage module 314, and microtomy module 307 as opposed to manually transferring the slides or other tissue holders, offers certain potential advantages. For one thing, it may free personnel from the necessity of having to performing these sometimes repetitive or tedious operations manually. Advantageously, this may allow the personnel to perform more value-added operations and/or other operations less amenable to automation. For another thing, the transport module may be better suited for performing these operations faithfully and timely than the personnel, who may at times be distracted with other tasks, or forget or be unable to perform these operations faithfully or timely. In particular, manual transport by personnel may result in missed slides, slide breakage during handling, misplacement or misreading of slides by the imager. In addition, in the case of slide storage, transport by personnel to the storage module can result in misplaced slides, incorrect documentation of slides stored within the storage module and/or costly and lengthy slide retrieval from the storage module. Advantageously, automated transport of the slides may allow improved productivity or throughput by reducing instrument downtime waiting for samples to be transferred manually. Similar advantages can be offered by automating the transfer of tissue blocks between microtomy module 307 and storage module 314.

In one embodiment, transport module 302 may be a robotic device capable of transporting a slide between stations. In one embodiment, transport module 302 may be an X-Y-Z robotic device dimensioned to transport one or more slides between stations. Representatively, transport module 302 may be a track and elevator system. The track system may be a conveyor belt or plate system that transports the slide horizontally in an "x-" direction. In this aspect, one or more slides may be placed on the conveyor and conveyed between the desired stations, for example, between coverslipper module 306, imager 308 and storage module 314. In one embodiment, the conveyor belt system may have two separate conveyor belts such that one conveyor belt transfers the slide in one direction and the other conveyor belt transfers the slide in the opposite direction as illustrated by arrow 316. Alternatively, as described with reference to FIGS. 4-9, a single conveyor belt system may be used to transport the slide in more than one direction. Transport module 302 may further include an elevator device. The elevator device transports the slide vertically in a y-direction when it is desired that a slide be positioned at a location above or below the conveyor belt. The elevator device may further include a component for transporting the slide in and out of the elevator in the z-direction.

Staining module 304 and coverslipper module 306 may be an integrated slide stainer and coverslipping system. Alternatively, staining module 304 and coverslipper module 306 may be in separate instruments at different locations. In the case of an integrated system, staining module 304 and coverslipper module 306 may be a staining/coverslipping system such as the TISSUE-TEK® PRISMA® and TISSUE-TEK® GLAS™ g2 combo system or TISSUE-TEK® PRISMA® and TISSUE-TEK® FILM® combo system commercially available from Sakura Finetek U.S.A., Inc., Torrance, Calif.

In one embodiment, staining module 304 may have hematoxylin and eosin stain (H&E) and special staining (SS) capabilities. At H&E/SS staining and coverslipping, the biological sample may undergo H&E or SS staining and optional coverslipping. Other staining or testing protocols also can be performed.

During operation, an individual slide or group of slides placed in a basket may be loaded into staining module 304 and stained according to a desired staining protocol. In the case of a group of slides, the staining protocol can be the same for all slides or selected from a staining protocol menu, either by an operator or automatically by reading a bar code, an RFID or any other protocol identification device. Once the staining protocol is complete, the slide or group of slides within the basket is automatically transferred to coverslipper module 306 for individual cover slipping. The identifier associated with each slide is then read as the slides are coverslipped and either placed as a group in a basket or individually fed onto transport module 302.

In an alternative embodiment, where a group of slides are stained together, the slides may be singulated (separated from the group) in staining module 304 and placed on transport module 316. For example, where a group of slides are stained together in a basket, a pick and place robotic device in staining module 304 may transfer the slides individually to transport module 316. From transport module 316, the slides may be conveyed to coverslipper module 306, or, without a coverslip, to one of imagers 308, 310, 312 or to storage module 314.

Imaging methods (quick-scan, 20×, 40×, z-stack, etc.) at imagers 308, 310, 312 can be pre-assigned to each slide according to a laboratory default or specific instructions from, for example, a pathologist. In the case of basket-grouped slides, in one embodiment, each of the slides would be assigned the same scanning method(s). Individual slides or the basket of slides may be assigned to one of imagers 308, 310, 312 based on the imagers availability or according to laboratory defined rules, such as dedicating one or more imagers to a specific scanning method (e.g., quick-scan, 20×, 40× or z-stack) or a plurality of methods.

In one embodiment, a slide including a biological sample is individually transported by transport module 302 to one of imagers 308, 310, 312 and/or storage module 314. If the slide is ready for imaging (e.g., dry), the system checks to see if, for example, imager 308 is available. Imager 308 is determined to be available if, for example, it is properly functioning and not currently imaging another sample on a slide. If imager 308 is not available, the availability of imager 310 is determined. If imager 310 is not available, the availability of imager 312 is determined. This process continues, until an available imager is found. Alternatively, an imaging schedule between the slide and a particular imager may be predetermined. Representatively, information relating to a period of time sufficient to allow the slide to dry may be assigned to the slide and imagers 308, 310 and 312 may be on an imaging schedule. The system may determine which imager will be available after the drying period expires. Once an available imager is determined, the slide is transported by transport module 302 to the available imager. Although three imagers are illustrated in FIG. 3, it is contemplated that fewer than three or more than three imagers may be included in system 300.

If none of imagers 308, 310, 312 are available or there are other conditions which require delay in imaging (e.g., waiting for slide processing instructions), transport module 302 transports the slide to storage module 314. The slide remains in storage module 314 until one of imagers 308, 310, 312 become available and/or processing instructions are received. Once an imager is determined to be available, the slide is transferred from storage module 314 to transport module 302 using, for example a robotic device, and transported by transport module 302 to the available imager for imaging. Upon completion of imaging, the slide may be transported by transport module 302 from imager 308, 310 or 312 to storage module 314. The image may be communicated to a diagnostician, for example a pathologist, for immediate examination. Via a computer (e.g., a personal computer), the pathologist can then examine an image of a sample on a slide for viewing and recall a slide for more imaging work if desired. Alternatively, if it is determined that no further examination of the slide is desired, the slide may be removed from the storage module 314.

In one embodiment, storage module 314 may include more than one storage module. In this aspect, one or more of the storage modules may act as short-term storage areas for slides likely to need more imaging work. In addition, one or more of the storage modules may act as long-term storage areas for slides which are unlikely to require more imaging work in the near future. The long-term storage modules may be located within the laboratory or remotely.

In one embodiment, storage module 314 is configured to group slides (and tissue blocks for the block storage system) according to user-defined criteria. For example, slides pertaining to a patient case could be placed in the same area. Then cases or blocks can be located by date of production, by physician, by provenance, or by a combination of these criteria. Representatively, as noted above, a slide may contain an identifier that may be read by a reader (e.g., RFID reader, bar code reader). That identifier (e.g., RFID, bar code) may contain information (e.g., letters, numbers and/or symbols) indicating a date of production, a physician and/or a provenance. When the information is read by a reader, the information may be sent to the controller 400 or to other devices through the communications infrastructure.

Automated system 300 as illustrated in FIG. 3 provides fully automated movement of slides between staining module 304, coverslipper module 306, imagers 308, 310, 312 and storage module 314. In this aspect, system 300 provides a seamless and continuous workflow which is in sync with other laboratory processes and eliminates the need for overnight processing and batching while reducing personnel errors and liabilities. It is further noted that there are no touch points from staining to storage in system 300 therefore system 300 is believed to satisfy even the most stringent quality control programs such as Lean and Six Sigma.

Figure 4:
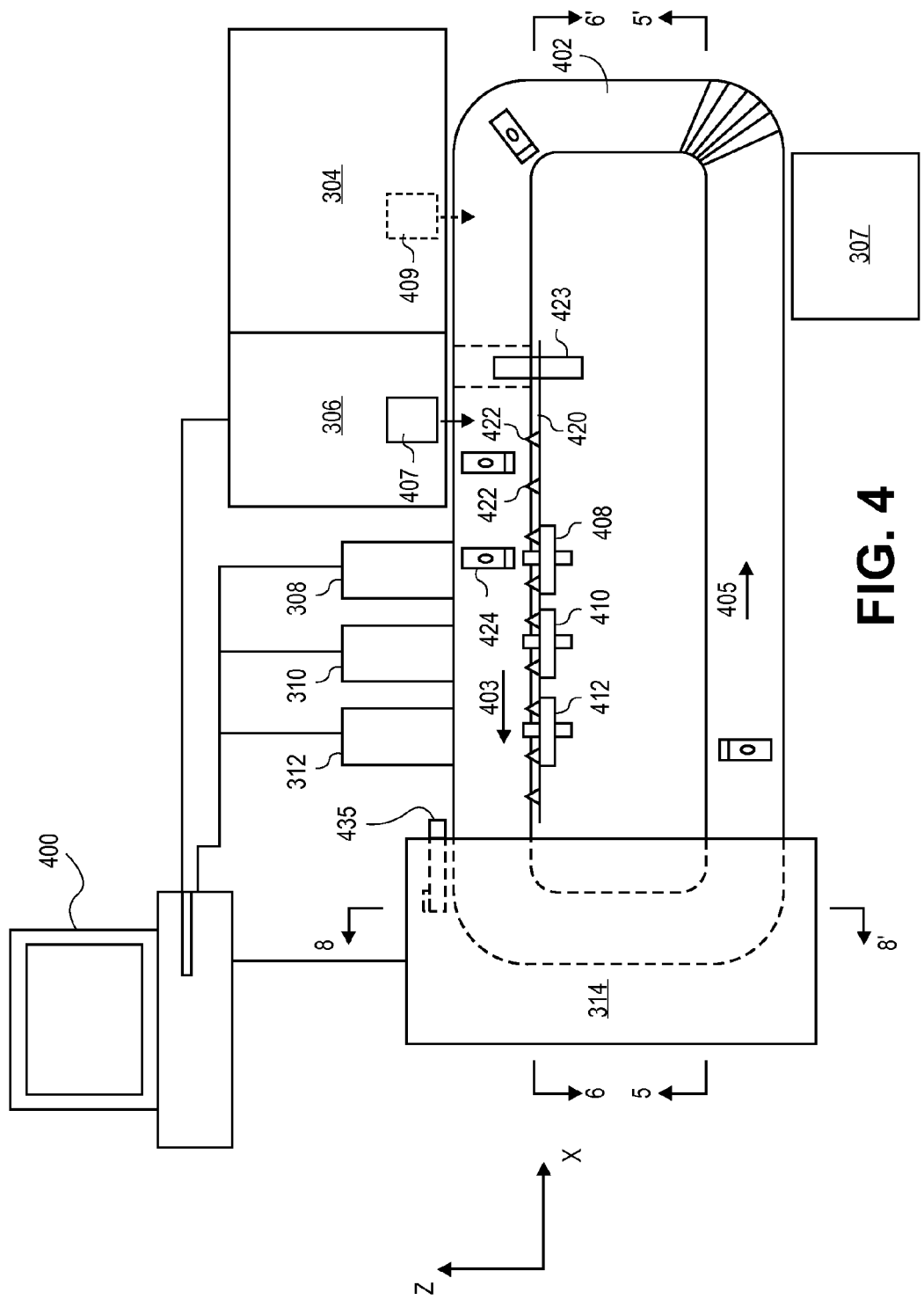
FIG. 4 illustrates a top view of one embodiment of an automated system for processing biological specimens.

FIG. 4 illustrates an embodiment of the system of FIG. 3. In this embodiment, stainer module 304 is a TISSUE-TEK® PRISMA®stainer and coverslipper module 306 is a TISSUE-TEK® FILM® coverslipper, both commercially available from Sakura Finetek USA. The TISSUE-TEK® PRISMA® stainer module and TISSUE-TEK® FILM® coverslipper module may be connected to one another and a loading container used in the coverslipper module to hold one or more racks of slides prior to a coverslipping operation may move between the coverslipper module 306 and stainer module 304. A brief description of the interaction between these modules is presented in the following paragraphs.

In order to automate the movement of the loading container in the coverslipper module 306 between coverslipper module 306 and stainer module 304, software instructions and a data link between coverslipper module 306 and stainer module 304 are provided. Such instructions and link may be solely between coverslipper module 306 and stainer module 304. Alternatively, a control system may be connected to each of strainer module 304, coverslipper module 306, imagers 308, 310, 312, storage module 314 and transport module 302 that may be used to transport a slide between imagers and the modules. FIGS. 4-9 describe controller 400 connected to each of the noted modules and imagers. In such case, instructions regarding the transfer and a data link may be established between the modules and imagers and the control system. In such case, controller 400 may control the transfer operations between stainer module 304 and coverslipper module 306. Controller 400 may also control (e.g., direct operation of) the various other modules and imagers as well as control slides relative to the modules and imagers.

Referring again to movement of a loading container from stainer module 304 to coverslipper module 306, the loading container sits on a plate that is connected to wires that move the plate and the loading container in an x- and y-direction, respectively, by two-step motors. The plate may move the loading container in an x-direction into the stainer.

In operation, a transfer arm of stainer module 304 retrieves a rack of slides and moves the rack along an xy axis to one or more individual staining stations. The transfer arm transfers a rack of slides to an appropriate staining station and then lowers the rack into that staining station for staining (a z-direction). Following staining, the transfer arm removes the rack of slides from the staining station and moves in x- and y-direction to another staining station or, when all staining operations are complete, to a transfer station where the rack of slides is to be transferred from the stainer to the Film® coverslipper module (coverslipper module 306).

For a transfer operation between stainer module 304 and coverslipper module 306, the loading container in coverslipper module 306 receives instructions to move from coverslipper module 306 to stainer module 304 through the adjacent doorways in each device. The loading container is moved by the plate on which it sits along a single plane (xy plane) from the coverslipper to a position inside the stainer adjacent the doorway of the stainer module. Once inside the stainer module, the transfer arm lowers the rack of slides into the loading container. The loading container typically contains a solution such as xylene that wets the slides. The loading container then moves on the x-direction plate from the stainer into the coverslipper again through the adjacent doorways. A cover slipping operation including placing a film-type cover slip on individual slides in the basket of slides is then performed in the coverslipper.

Transport module 302 may be a robotic device capable of transporting a slide between stations. In the embodiment shown in FIG. 4, transport module 302 may be a robotic device including conveyor 402 that is a conveying system to transport a slide or group of slides horizontally in a loop between stainer module 304/coverslipper module 306, imagers 308, 310, 312 and storage module 314. In this embodiment, conveyor 402 transports a slide in one direction as illustrated by arrow 403 from stainer module 304 or coverslipper module 306 to imagers 308, 310, 312 and to storage module 314 and in an opposite direction as illustrated by arrow 405 from storage module 314 to imagers 308, 310 and 312. In one embodiment, conveyor 402 may be a conveyor belt or a set of conveying pallets disposed in a horizontal plane and dimensioned to transport a slide or group of slides. A conveying system that is a set of conveying pallets may be similar to systems currently used in luggage carousels at commercial airports. Such carousels typically include a deck that is surrounded by support wheel tracks. The support wheel tracks define a path that is frequently oval shaped. Evenly spaced along the wheel tracks are pallet support members. Attached to each end of the pallet support members are support wheels. The support members are configured to be transported along the support wheel tracks by the rolling of the support wheels. The support members are connected to each other at the top by straps that run between support members. The bottoms are connected to each other by rigid links. Thus, the support members, the support wheels, and the straps function in a manner analogous to a train on endless railroad tracks.

Attached to the pallet support members are pallets. The pallets are designed to overlap one another and are secured to the pallet support members to form a flexible surface. The overlap configuration of the pallets allows them to slide relative to each other as the pallets travel around the corners of the tracks. The leading edge of the pallets are secured to the support members by fasteners. Each of the pallets may have a slight bend to negotiate the curves in the unit.

In the embodiment shown in FIG. 4, conveyor 402 receives a slide from coverslipper module 306 and conveys the slide to one of imagers 308, 310, 312. Referring to the TISSUE-TEK® FILM® coverslipper, coverslipper module 306 individually places a film strip on a slide. With the system described in reference to FIG. 4, the slide is then moved to a discharge position in coverslipper module 306 and discharged onto conveyor 402 from coverslipper module 306 onto conveyor 402. A discharge position in coverslipper module may be established at a position downstream of the coverslipping operation. Referring to FIG. 4, a slide, such as slide 424, is discharged onto conveyor 402 in a manner that its length dimension is disposed across a width dimension of conveyor 402. Reader 423, such as an RFID or bar code reader, may be positioned at a discharge point onto conveyor 402 or downstream from a discharge point to read an identifier on slide 424. Reader 423 is connected to controller 400 to indicate to controller 400 that slide 424 is on conveyor 402. Once delivered to conveyor 402, conveyor 402 conveys slide 424 toward imagers 308, 310, 312.

As noted earlier, in this embodiment, multiple slides are brought to coverslipper module 306 from stainer module 304 in a rack. In coverslipper module 306, the slides are singulated (separated from other slides in a rack) for coverslipping. In one embodiment, all stained slides in coverslipper module 306 are coverslipped. In another embodiment, a coverslipping operation may be bypassed. Such bypass can occur at the singulation point in coverslipper module 306. According to this embodiment, a slide is singulated and either directed to be directly discharged onto conveyor 402 or to be coverslipped and then discharged.

In one embodiment, a slide retaining device is positioned adjacent to or connected to conveyor 402. Slide retaining device 420, in one embodiment, is an oval-shaped chain or belt (e.g., a continuous loop) having projections 422 extending outwardly therefrom. Projections 422 are spaced from one another at approximately a width of a slide.

As shown in FIG. 4, stainer module 304, coverslipper module 306 and imagers 308, 310, 312 are positioned on one side of conveyor 402. Slide retaining device 420 is positioned on a side of conveyor 402 opposite to the side including stainer module 304, coverslipper module 306 and imagers 308, 310, 312. Projections 422 of slide retaining device 420 project outward in a direction toward conveyor 402. A length of slide retaining device 420 is positioned adjacent conveyor 402 so that projections 422 extend a distance on to conveyor 402. In one embodiment, slide retaining device 410 is a synthetic rubber or other plastic material with projections 422 of similar preferably resilient material. Projections 422 have a thickness of 0.5 millimeters (mm) or less, such as 0.25 mm, and a length of 0.5 mm to 1 mm. Slide retaining device 420 projects above the plane defined by conveyor 402 a distance sufficient to allow a length of projections 422 to lay on conveyor 422 or slightly above (e.g., less than 0.25 mm above) conveyor 402. In this manner, a slide may be retained on conveyor 402 between two adjacent projections 422.

Figure 5:
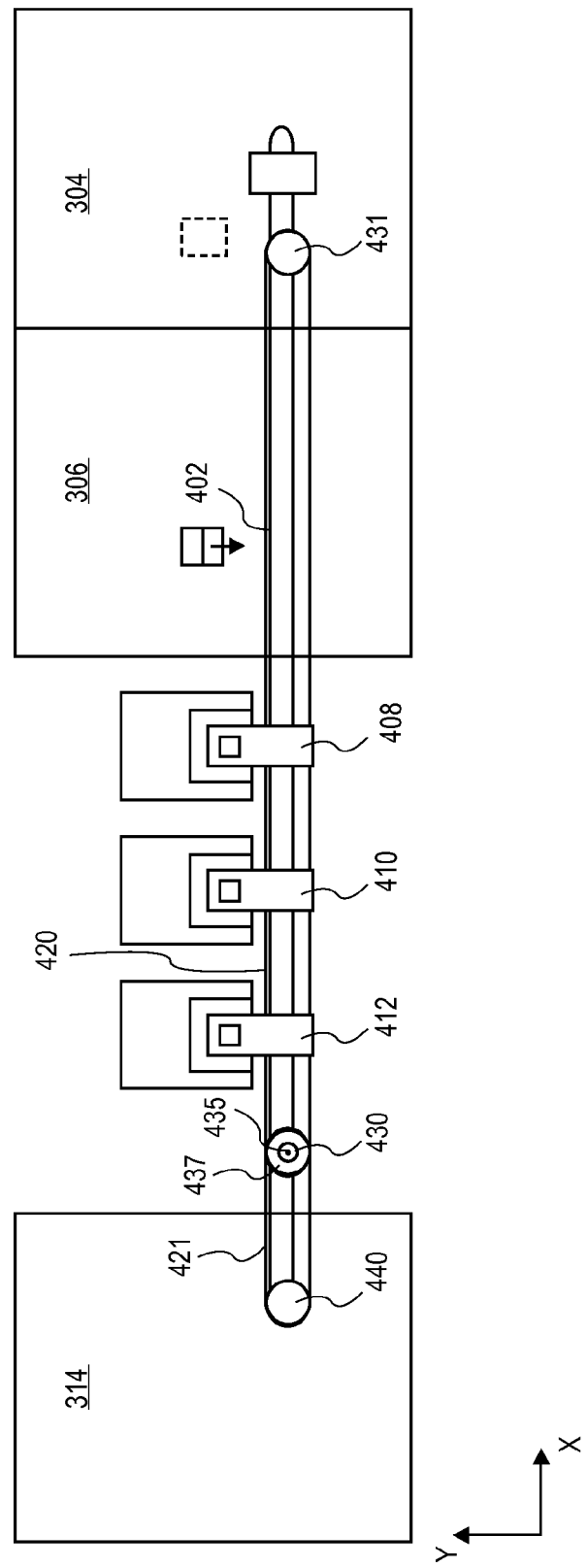
FIG. 5 illustrates a side view of the automated system of FIG. 4 through line 5-5'.

Slide retaining device 420 is rotated by a pulley and moves at the same rate as conveyor 402. FIG. 5 shows a side view of the system of FIG. 4 through line 5-5'. As shown in FIG. 5, slide retaining device 420 is connected at one looped end to pulley 430 and the other looped end to pulley 430. Pulley 430 rotates on axle 435. Axle 435 extends a width of conveyor 402 to an opposite side where a second end of axle 435 is connected to pulley 437. Pulley 437 is connected through a belt to pulley 440 that drives conveyor 402.

As illustrated in FIGS. 4-6 and 7, slides, such as slide 424 are discharged from coverslipper module 306 or optionally stainer module 204 individually and are placed on conveyor 402. Conveyor 402 may be positioned, for example, slightly below exit port 407 of coverslipper module 306 (and optional exit port 409 of stainer module 304) so that slides are placed onto conveyor 402 via gravity. Ideally, a slide is placed on conveyor 402 between two projections 422 of slide retaining device 420. However, where a slide is not aligned between projections 422 as the slide exits coverslipper module 306, a force of a projection against an edge of a slide is sufficient to re-position a slide between projections.

Conveyor 402 transports a slide to imagers 308, 310, 312. Imagers 308, 310, 312 are, for example, digital imagers and may further each contain a reader (e.g., RFID reader, bar code reader) connected with controller 400 to read an identifier on a slide indicate to controller 400 that a slide is in the imager and to associate a digital image with the identifier. In one embodiment, conveyor 402 stops at each imager and controller 400 assesses the availability of the imager (e.g., receives a signal that indicates whether or not an imager is available). If an imager is available and control system (e.g., controller 400) determines that a slide may be imaged at this time (e.g., the slide is dry), the slide is placed in the imager.

In one embodiment, a slide is placed in an imager by applying a pushing force to the slide. In this embodiment, associated with each imager 308, 310, 312 and controlled by controller 400 is a plunger assembly. FIGS. 4-7 show plunger assembly 408, 410 and 412 associated with imagers 308, 310, 312, respectively. Plunger assembly 408, 410 and 412 are positioned on a side of conveyor 402 opposite imagers 308, 310 and 312.

Each plunger assembly 408, 410, 412 includes an actuator such as an electrical motor or air piston that drives a corresponding plunger to extend or retract. A plunger, when actuated, moves outward from the plunger assembly toward the respective imager. The plunger may be a bar or rod having a thickness equivalent to or greater than a thickness of a slide. Each plunger assembly is positioned adjacent conveyor 402 such that when a plunger is extended from a plunger assembly, the plunger will contact a surface of conveyor 402 or extend over conveyor 402 a slight distance (e.g., 0.1 to 0.25 mm). Plunger must be close enough to conveyor 402 that it is capable of contacting an edge of a slide on the conveyor and pushing the slide off conveyor 402 as it extends. To the extent a height of slide retaining device 420 would otherwise prevent a plunger form contacting an edge of a slide, plunger is made of a material having sufficient weight or density to deflect slide retaining device 420. For example, a plunger comprised of a steel bar or rod can be made of a sufficient weight to deflect slide retaining device 420 of a synthetic rubber belt downward. In another embodiment, a plunger may extend from a plunger assembly at an angle slightly less than horizontal (e.g., less than 5°) so that the plunger will deflect slide retaining device 420 to be at most parallel with a surface of conveyor 402.

Figure 7:
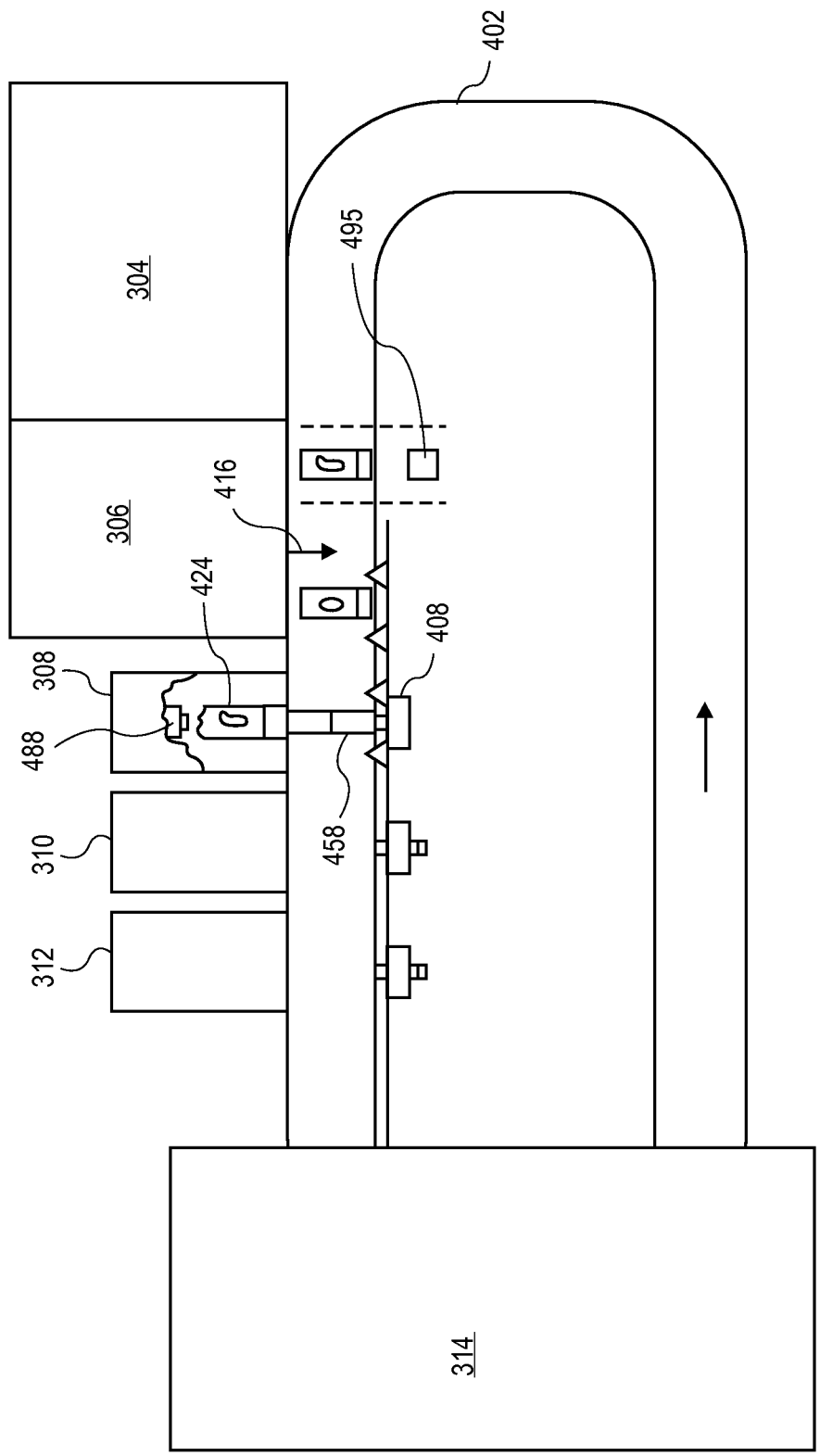
FIG. 7 illustrates a top view of the automated system of FIG. 4 showing a slide placed in an imager.

If a slide is positioned in front of the imager (imagers 308, 310, 312) and the imager is available, the plunger will push the slide into imager. Thus, the plunger is oriented such that it will contact an edge of a slide on conveyor 402. FIG. 7 shows an illustration of a slide pushed from conveyor 402 into imager 308. FIG. 7 shows plunger 458 actuated from plunger assembly 408 and extending across conveyor 402. The actuation of plunger 458 causes plunger 458 to contact slide 424 and push slide 424 into imager 308. A cut-away view of imager 308 shows slide 424 on a stage or imaging platform within imager 308 and ready for imaging. The cut-away view also shows plunger assembly 488 on a side of a stage or imaging platform opposite plunger assembly 488. Plunger assembly 488 is configured to push slide 424 from inside imager 308 back onto conveyor 402 once imaging of slide 475 is complete.

As noted above, in one embodiment, controller 400 is connected to stainer module 304, coverslipper module 306, imagers 308, 310, 312, plunger assemblies 408, 410, 412, corresponding plunger assemblies associated with each imager, storage module 314 and conveyor 402. In addition to optionally controlling a staining of slides in stainer module 304 and coverslipping slides in coverslipper module 306, controller 400 includes instructions (e.g., a computer program) for controlling a discharge of a slide from coverslipper module 306 or, optionally, stainer module 304 onto conveyor 402 and the movement of conveyor 402 to bring a slide to imagers 308, 310, 312.

To control discharging of a slide onto conveyor 402 from coverslipper module 306, controller 400 receives data from coverslipper module 306 whether a slide is ready for discharge. In one embodiment, this data is provided to controller 400 in the form of a signal when a slide is positioned in a designated area in coverslipper module 306. The slide may or may not have proceeded through a coverslip operation in coverslipper module 306. Controller 400 checks to see if a position on conveyor 402 is free to receive a slide. In the embodiment shown in FIGS. 4-7, the system includes sensor 495 positioned approximately one slide width upstream of exit port 416 of coverslipper module 306. Sensor 495 may be, for example, a photoelectric sensor that sends a light beam across a surface of conveyor 402. When the beam is broken, a sensor sends a signal to controller 400 that a slide is present. It is appreciated that, in an embodiment where a slide may be discharged from stainer module 304, a similar technique may be employed with, for example, a sensor similar to sensor 495.

Figure 6:
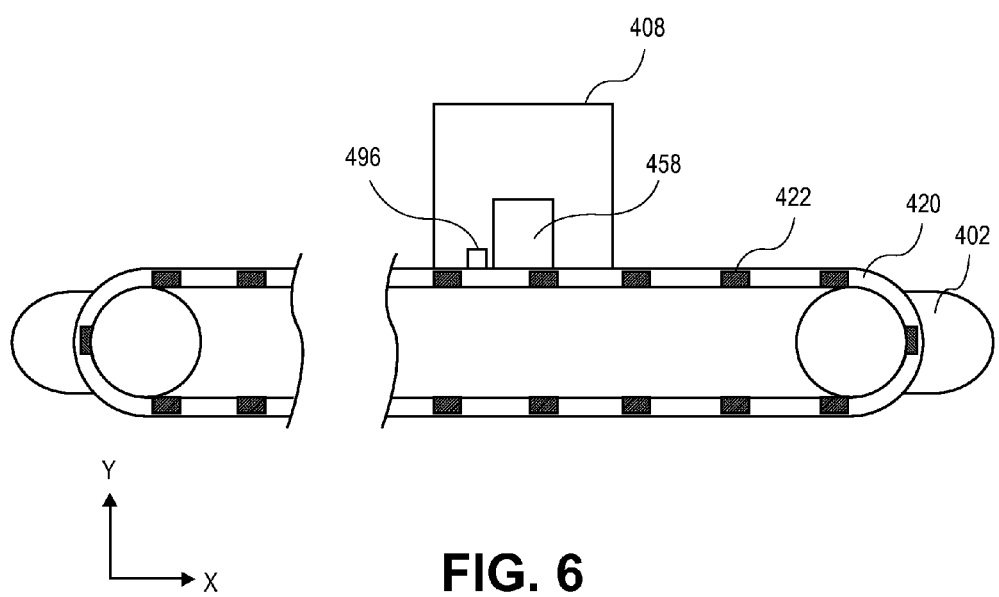
FIG. 6 illustrates a side view of the automated system of FIG. 4 through line 6-6'.

In one embodiment, control system stops conveyor 402 for a brief moment (e.g., three to five seconds) in periodic intervals each time a slide could be positioned in front of an imager. Controller 402 receives a signal whether the imager is available for receiving a slide for imaging. It may receive this signal in an unsolicited fashion (e.g., a sensor associated with the sensor sends a signal whenever the imager is available) or it may solicit the signal (e.g., controller sends a signal to a sensor associated with the imager and receives a reply to the sent signal from the sensor). If a slide is present on conveyor 402 and an imager is available, control system will activate a corresponding plunger assembly to place a slide in the imager. Similarly, controller 400 checks when an imaging of a slide is complete and subsequently discharges the slide onto conveyor 402. In one embodiment, a sensor such as a photoelectric sensor may be associated with, including connected or adjacent to, each of plunger assembly 408, 410, 412 to sense whether a slide is present on conveyor 402 or conveyor 402 is free to receive a slide from imagers 308, 310, 312. FIG. 6 shows sensor 496 connected to imager 408. In one embodiment, a corresponding sensor component may be connected to imager 308 directly across from sensor 496. Alternatively, a memory associated with controller 400 may track the position of slides on conveyor 402 based on data supplied by sensor 495 and by coverslipper module 306, and with this data, compute whether conveyor 402 is free to receive a slide from imagers 308, 310, 312. The brief stoppage of conveyor 402 also may be utilized to assess whether a slide is on conveyor 402 upstream of an exit port of coverslipper module 306, such as based on data received from sensor 495.

Although plunger assemblies are described for transferring slides between conveyor 402 and imagers 308, 310, 312, it is contemplated that any other type of robot device suitable for transferring a slide between processing stations may be used. Representatively, a robotic arm capable of grasping slide 424 and transferring slides between imagers 308, 310, 312 and conveyor 402 may be used. For example, in embodiments where a group of slides are transported within a basket, slides must be removed individually from the basket for imaging. In this aspect, a Gantry or Cartesian coordinate type robot, a selective compliant assembly robot arm (SCARA) type robot, an articulated arm type robot, or a combination thereof (e.g., a SCARA type robot coupled in a Gantry type robot configuration) may be used to retrieve and deposit individual slides within the basket.

In one embodiment described with reference to FIGS. 3-7, stainer module 304 and coverslipper module 306 are connected and slides are conveyed by stainer module 304 to coverslipper module 306 through a commercially available integrated system, although in another embodiment, such conveyance can alternatively be controlled by controller 400 as part of an overall control system. In another embodiment, slides may be transferred from stainer module 304 to conveyor 402 and then conveyed via conveyor 402 to coverslipper module 306 using, for example, a plunger assembly(ies) such as described above or other type of transfer mechanism.

FIGS. 4-7 also show conveyor 402 extending into storage module 314. In one embodiment, conveyor 402 has a continuous loop shape with one end of the loop extending into and out of storage module 314.

Figure 8:
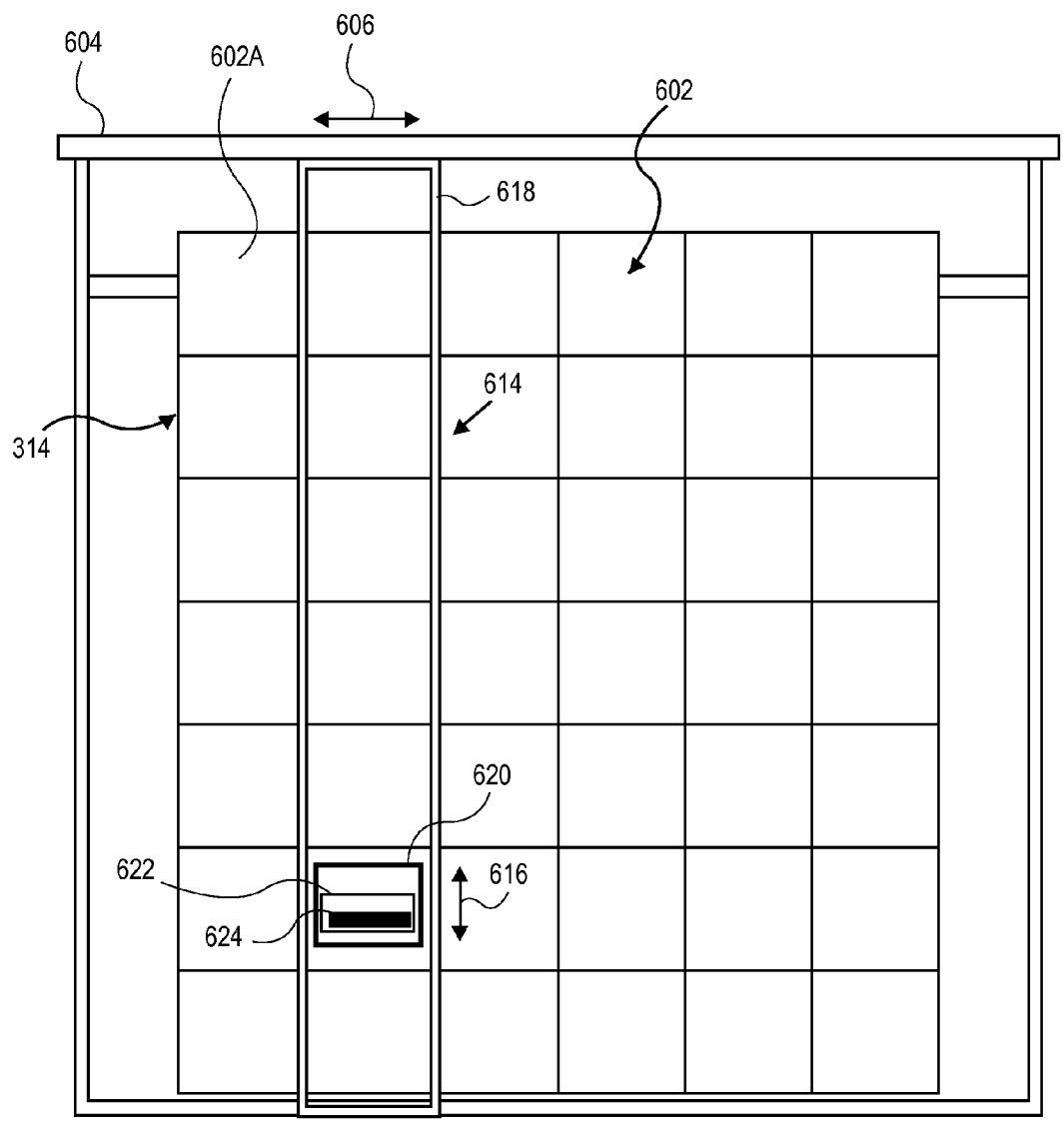
FIG. 8 illustrates a side view of the automated system of FIG. 4 through line 8-8'.

FIG. 8 illustrates a cross-section of storage module 314 through line 8-8' of FIG. 4. In one embodiment, storage module 314 may include at least one of a drawer, chamber, compartment, cabinet, enclosure, cubbyhole, or the like. A robotic device such as transport module 302 may be capable of introducing a slide into storage module 314, and removing the slide from storage module 314, for example, via conveyor 402. Storage module 314 may further include a door which may be accessed by transport module 302.

In an embodiment where storage module 314 is a cabinet, storage module 314 may have a plurality of slide stations 602. Each of slide stations 602 may be dimensioned to receive and store a slide. In one embodiment, slide stations 602 are dimensioned to receive and store a slide individually or a group of slides. In the case of a group of slides, the slide group may be stored in slide stations 602 in a tray or basket. For example, a tray or basket holding 10 slides may be stored within one of slide stations 602. In this aspect, slide stations 602 are dimensioned to store the tray or basket having the sides therein.

In one embodiment, stations 602 may be formed in a grid pattern as illustrated in FIG. 8. Slides stored within stations 602 may be located and retrieved from storage 314 using an indexing system including, for example, coordinates corresponding to the grid pattern. Representatively, each column may be assigned an identifier and each row may be assigned a different identifier from that of the columns. For example, the first column starting from the left hand side of storage module 314 may be assigned the identifier "1" and the first row starting at the top of storage module 314 may be assigned the identifier "A." In this aspect, the location of station 602A may be A1. A slide stored within station 602A may be assigned location A1. When it is desired to retrieve the slide, the system is directed to retrieve the slide at location A1. In other embodiments, slide stations 602 may be vertically stacked compartments within storage module 314.

Transport module 302 may include one or more elevator devices positioned in storage module 314 to place slides within or retrieve slides from slide stations 602 and transfer slides between slide stations 602 and conveyor 402.

Elevator device 614 may be used to move the slide vertically between conveyor 402 (a y-direction in reference to FIG. 4). Elevator device 614 also includes track member 604 which allows for movement of frame member horizontally in a z-direction (with reference to FIG. 4) as illustrated by arrow 606. Elevator device 614 may be positioned between conveyor belt 402 and slide stations 602. Elevator device 614 may include frame member 618 and lift member 620 which travels along frame member 618. A motor and pulley system may be connected to frame member 618 and lift member 620 to drive lift member 620 along frame member 618.

Elevator device 614 may further include slide platform 622 positioned within lift member 620. Slide platform 622 may be movably coupled to lift member 620 such that it slides horizontally in an x-direction to eject the slide from or receive the slide within elevator device 614. Slide platform 622 is dimensioned to receive and retain slide 624 within lift member 620. In one embodiment, slide platform 622 may be a rectangularly shaped box having open ends and of a size configured to contain a single slide (e.g., 1 in.×1 in×3 in.). Slide platform 622 may be at least as wide as a width of the slide so that the slide may be positioned thereon. The slide may be inserted into and retrieved through either side of slide platform 622. Alternatively, slide platform 622 may be a planar member (a true platform) upon which the slide can be supported by slide platform 622.

Elevator device 614 may be used to transfer slide 624 between conveyor 402 and slide stations 602. Representatively, conveyor 402 may transport slide 624 from, for example, coverslipper module 306 or imagers 308, 310, 312, to slide stations 602. Conveyor 402 moves slide 624 horizontally in the x-direction until slide 624 is aligned with slide platform 622. In this aspect, lift member 620 moves vertically in the y-direction along frame member 618 until slide platform 622 is aligned with slide 624. Once slide platform 622 is aligned with slide 624, slide platform 622 moves in the x-direction toward conveyor 402 until it is positioned around slide 624. In one or more embodiments, slide platform 622 may include pincers, claws, jaws, hook-like structures or another gripping member. Slide platform 622 then moves in the opposite direction (i.e., away from conveyor 402) with slide 624 inside. Lift member 620 raises slide platform 622 having slide 624 therein until slide 624 is aligned with opening 428 of slide stations 602. Slide platform 622 then moves in the "X" direction toward slide stations 602 to insert slide 624 within the opening of the slide station. Once slide 624 is within the opening, slide platform 622 releases slide 624 and retracts (i.e. moves away from slide stations 602) thereby leaving slide 624 within slide stations 602 for storage.

Once storage is complete, elevator device 614 may be used to remove slide 624 from slide stations 602 and place it back on conveyor 402 for transport to, for example, imagers 308, 310, 312.

Although elevator device 614 is described for transferring slide 624 between conveyor 402 and slide stations 602, it is contemplated that any other type of robot device suitable for transferring a slide between processing stations may be used. Representatively, a robotic arm capable of grasping slide 624 and transferring slide 624 between slide stations 602 and transport module 302 may be used. For example, in embodiments where a group of slides are transported within a basket, slides must be removed individually from the basket for imaging. In this aspect, a Gantry or Cartesian coordinate type robot, a selective compliant assembly robot arm (SCARA) type robot, an articulated arm type robot, or a combination thereof (e.g., a SCARA type robot coupled in a Gantry type robot configuration) may be used to retrieve and deposit individual slides within the basket.

As previously discussed, a slide may be inserted and stored in any of stations 602 which are positioned in a grid pattern. In this aspect, the robotic device for inserting and retrieving the slides must be able to move both vertically in the y-direction and horizontally in the x-direction. To store a slide or retrieve a slide stored in station 602A, lift member 620 of elevator device 614 moves vertically as illustrated by arrow 616 up to the top row (e.g. row A) of storage module 314. Frame member 618 then moves horizontally as illustrated by arrow 606 to the first column (e.g., column 1).

To store slide 424 within station 602A, slide platform 422 moves in the "z-" direction toward storage module 314 and inserts slide 424 within station 602A. Once slide 424 is positioned within station 602A, slide platform 622 moves in a direction away from storage module 314 leaving slide 624 behind within station 602A. To retrieve slide 624 from station 602A, slide platform 622 is inserted within station 602A and around slide 624. Movement of slide platform 622 away from station 602A pulls slide 624 out of station 602A and into elevator device 614. Lift member 620 of elevator device 614 may then be raised or lowered to transfer slide 624 to conveyor 402. Conveyor 402 may then be used to convey slide 624 to imager 308, 310, 312.

The identification, placement and retrieval of a slide within storage module 314 may be controlled by controller 400 that is electrically or communicatively linked to transport module 302. In one or more embodiments, movement or operation of transport module 302 may be based on signals exchanged between the controller and storage module 312. For example, in one embodiment, such a controller may receive a signal from coverslipper module 306 indicating that a slide is ready for storage. In response, the controller may signal transport module 302 to retrieve the slide from the coverslipper module and transfer the slide to storage module 314. A reader (e.g., an RFID or bar code reader) may be positioned at the entrance to storage module to read an identifier associated with the slide. This information is transmitted to controller 400. The controller may identify an open slide station within storage module 314 and signal transport module 302 to insert the slide within the open slide station. The slide location information may be stored by the system. In one embodiment, the slide location may be selected based on a criteria such as patient case, a physician or hospital, term of storage, etc. When retrieval of the slide is desired, for example where a pathologist instructs the system to perform further imaging of the slide, controller 400 may determine the location information of the desired slide and signal transport module 302 to retrieve the slide from the appropriate slide station within storage module 314.

Figure 9:
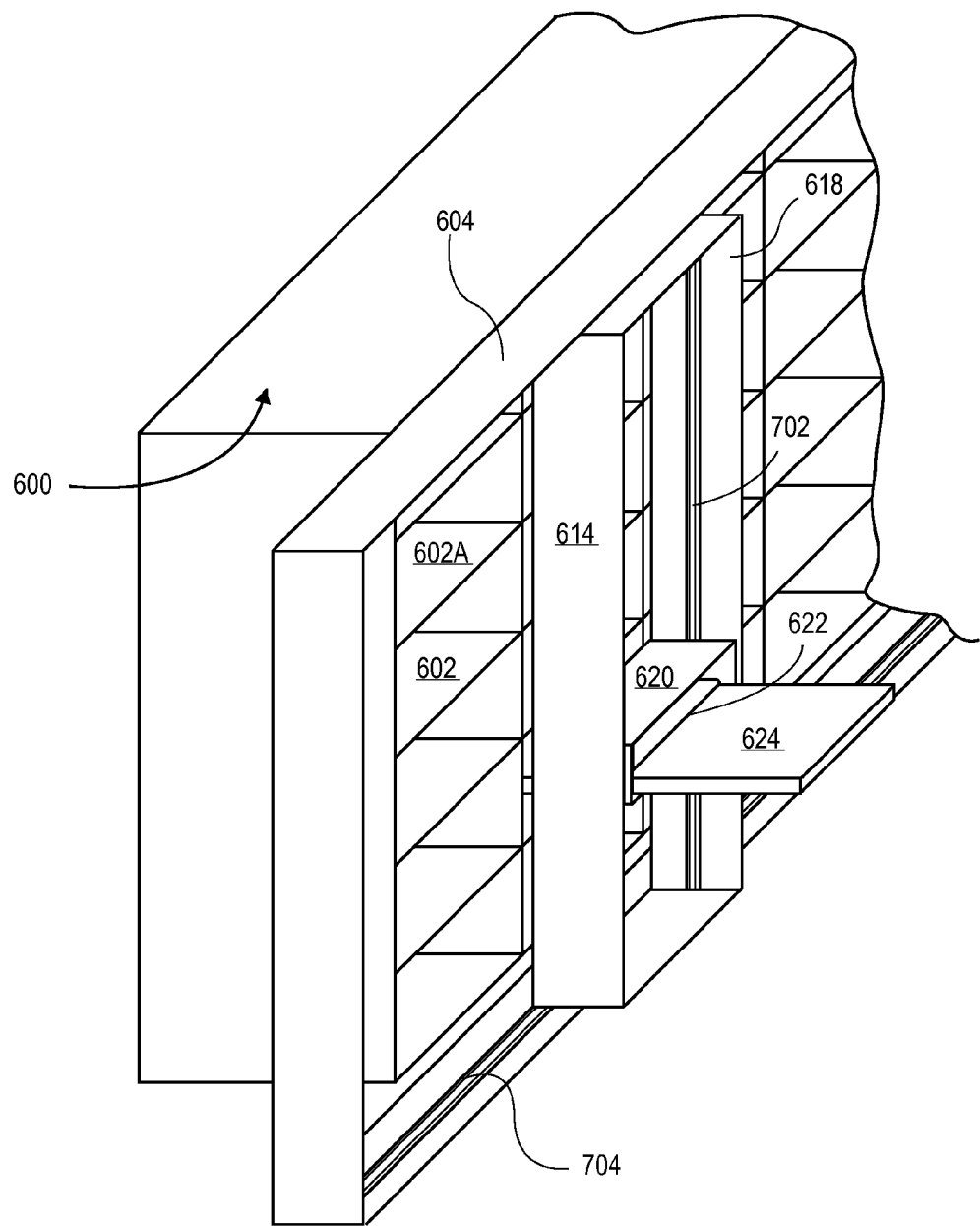
FIG. 9 shows a perspective view of an embodiment of a storage module of the automated system of FIG. 4.

FIG. 9 illustrates a perspective view of the storage module and elevator device of FIG. 8. From the view in FIG. 9, it can be seen that lift member 620 slides vertically along track 702 formed in lift member 620. In this aspect, lift member 620 may have protrusions along its outer surface that line up with and may be engaged within track 702. Similarly, track member 604 includes tracks 704 along which frame member 618 slides.

FIG. 8 and FIG. 9 describe a storage module in connection with storing slides. In another embodiment, a storage module is configured to store slides as well as tissue blocks (e.g., tissue blocks containing an identifier tag). In another embodiment, the system includes storage module 202 for storing slides and a separate storage module for storing tissue blocks. A storage module to store tissue blocks may be configured similar to storage module 314, including an identifier reader, and linked to controller 400. In either configuration, controller 400 is configured to store identification information of the slides and tissue blocks so that a slide(s) may be linked to a tissue block. FIG. 4 shows microtomy module 307 adjacent conveyor 402. Microtomy module may include tissue block processing equipment including a microtome and an identifier reader linked to controller 400. In one embodiment, tissue block may be loaded onto conveyor 402 from microtomy module 307 (or unloaded from conveyor 402 to microtomy module 307) or loaded/unloaded storage module 314 to conveyor 402 or vice versa similar to the methods discussed above for loading/unloading slides.

An automated system for slide transport between processing stations is disclosed. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well. Representatively, in one embodiment, a "Reflex Staining" procedure may be implemented. In that procedure, the system recommends specific staining and/or testing of biological samples based on pattern recognition reports of an interpretation module. The reflex stainer may include a staining system, imager and interpretation module, which are grouped together and implemented as a single automated instrument. Alternatively, they may be in separate instruments at different locations. Processing may be performed by instruments both inside and outside the reflex stainer, such as for example in grossing, processing and embedding, microtomy and staining and coverslipping.

In some embodiments, the above-described transport module may be implemented in connection with tissue block processing. Representatively, a sample of tissue, which has potentially been grossed and/or fixated in a block of paraffin, may be transported by the transport module between a microtome, imager and storage module. For example, the block having the tissue embedded therein and an identifier may be sectioned by the microtome and then transported to the storage module. If, upon examination of the tissue section, it is determined that another tissue section is needed, a controller may signal the transport module to retrieve the block from the storage module and transport it back to the microtome for additional sectioning.

One or more embodiments of the invention may be provided as a program product or other article of manufacture that may include a machine-readable computer medium having stored thereon one or more instructions. The medium may provide instructions, which, if executed by a machine such as a robot or integration unit, may result in and/or cause the machine to perform one or more of the operations or methods disclosed herein. Suitable machines include, but are not limited to, robots, integration units, computer systems, laboratory equipment, and a wide variety of other machines, to name just a few examples. Representatively, the medium may include recordable mediums, such as, for example, floppy diskette, optical storage medium, optical disk, CD-ROM, magnetic disk, magneto-optical disk, read only memory (ROM), programmable ROM (PROM), erasable-and-programmable ROM (EPROM), electrically-erasable-and-programmable ROM (EEPROM), random access memory (RAM), static-RAM (SRAM), dynamic-RAM (DRAM), Flash memory, other types of memory, other machine-readable medium within programmable logic units used to control robots, and combinations thereof.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

I claim:

1. A method comprising:
   processing at least one slide having a biological specimen thereon;
   automatically determining whether an imaging module is available for imaging of the biological specimen on the at least one slide;
   transporting the at least one slide to the imaging module using an automated transport module when it is determined that the imaging module is available; and
   transporting the at least one slide to a storage module using the automated transport module when it is determined that the imaging module is not available.

2. The method of claim 1, wherein processing comprises staining the biological specimen on the at least one slide.

3. The method of claim 1, wherein processing comprises applying a coverslip to the at least one slide.

4. The method of claim 1, wherein the imaging module is a first imaging module and determining further comprises:
   determining whether a second imaging module is available; and
   determining whether a third imaging module is available when the first imaging module and the second imaging module are not available.

5. The method of claim 4, wherein transporting comprises transporting the at least one slide to the second imaging module or the third imaging module using the automated transport module when the first imaging module is not available.

6. The method of claim 1 further comprising:
   transporting the at least one slide from the storage module to the imaging module using the automated transport module.

7. The method of claim 1 further comprising:
   indexing a location of the at least one slide within the storage module.

8. The method of claim 1 further comprising:
   imaging of the biological specimen on the at least one slide when the at least one slide is transported to the imaging module; and
   transporting the at least one slide to the storage module using the automated transport module after imaging.

9. The method of claim 8 further comprising:
   transporting the at least one slide from the storage module to the imaging module using the automated transport module for additional imaging.

10. The method of claim 1 further comprising:
    placing the at least one slide in the imaging module when the imaging module is available; and
    obtaining a digital image of the biological specimen on the at least one slide.

11. The method of claim 1, further comprising:
    retrieving a tissue block from the storage module; and
    transporting the tissue block to a microtomy module.

12. A system comprising:
    a processing module for processing at least one slide comprising a biological specimen thereon;
    an imaging module for imaging the biological specimen on the at least one slide;
    a storage module;
    a transport module for transporting the at least one slide between the processing module, the imaging module and the storage module; and
    a control module in communication with the transport module and at least one of the processing module, the imaging module and the storage module to control transport of the at least one slide,
    wherein the control module directs transport of the at least one slide to the storage module when the imaging module is not available or the slide is not ready for imaging.

13. The system of claim 12, wherein the control module directs transport of the at least one slide to the imaging module when the imaging module is available.

14. The system of claim 12, wherein the imaging module is configured to obtain a digital image of the specimen on the at least one slide.

15. The system of claim 14, wherein an image obtained by the imaging module is accessible at a remote station for analysis by a diagnostician.

16. The system of claim 12, wherein the imaging module comprises a plurality of imagers.

17. The system of claim 12, wherein the storage module comprises an indexing system for identifying a location of at least one slide stored therein.

18. The system of claim 17, wherein the control module is configured to identify the location of the at least one slide stored in the storage module and to direct the transport module to retrieve the at least one slide from the location.

19. The system of claim 12, further comprising a microtomy module, wherein the control module is in communication with the transport module to transport a tissue block to the microtomy module.

20. A machine readable medium including program instructions that when executed by a controller linked to at least one processing module, an imaging module, and a storage module, cause the controller to perform a method comprising:
- processing at least one slide having a biological specimen thereon at the one processing module;
- automatically determining whether an imaging module is available for imaging of the biological specimen on the at least one slide;
- transporting the at least one slide from the at least one processing module to the imaging module or the storage module; and
- retrieving the at least one slide from the imaging module or the storage.

21. The machine readable medium of claim 20, wherein retrieving the at least one slide from the storage module comprises determining a location of the at least one slide within the storage module.

22. The machine readable medium of claim 20, wherein the method further comprises transporting a slide other than the at least one slide from the storage module to the imaging module.

23. The machine readable medium of claim 20 wherein the method further comprises:
- transporting the at least one slide to the storage module;
- delivering the at least one slide to the storage module;
- assigning a location in the storage module to the at least one slide; and
- saving the location in a memory associated with the controller.

24. The machine readable medium of claim 20, wherein the method further comprises:
- retrieving a tissue block from the storage module; and
- transporting the tissue block to a microtomy module.

* * * * *